(12) United States Patent
Choi et al.

(10) Patent No.: US 11,197,635 B2
(45) Date of Patent: Dec. 14, 2021

(54) HEALTHCARE APPARATUS AND OPERATING METHOD THEREOF

(71) Applicant: SAMSUNG ELECTRONICS CO., LTD., Suwon-si (KR)

(72) Inventors: Ka Ram Choi, Seoul (KR); Hyo Sun Hwang, Seoul (KR); Jin Young Park, Hwaseong-si (KR); Jae Wook Shim, Yongin-si (KR); So Young Lee, Daejeon (KR); Sang Kon Bae, Seongnam-si (KR); Eui Seok Shin, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 371 days.

(21) Appl. No.: 16/200,765

(22) Filed: Nov. 27, 2018

(65) Prior Publication Data
US 2019/0167190 A1    Jun. 6, 2019

(30) Foreign Application Priority Data

Dec. 1, 2017   (KR) .................. 10-2017-0164566

(51) Int. Cl.
| | |
|---|---|
| *A61B 5/00* | (2006.01) |
| *A61B 5/026* | (2006.01) |
| *A61B 5/145* | (2006.01) |
| *A61B 5/1455* | (2006.01) |
| *A61B 5/0205* | (2006.01) |

(52) U.S. Cl.
CPC .......... *A61B 5/4866* (2013.01); *A61B 5/0261* (2013.01); *A61B 5/14532* (2013.01); *A61B 5/681* (2013.01); *A61B 5/0205* (2013.01); *A61B 5/1455* (2013.01); *A61B 5/7203* (2013.01); *A61B 5/7264* (2013.01); *A61B 2562/0219* (2013.01)

(58) Field of Classification Search
CPC ..... A61B 5/4866; A61B 5/681; A61B 5/0261; A61B 5/14532; A61B 2562/0219; A61B 5/7264; A61B 5/7203; A61B 5/1455; A61B 5/0205
See application file for complete search history.

(56) References Cited

U.S. PATENT DOCUMENTS

| | | |
|---|---|---|
| 9,504,393 B1 | 11/2016 | Rulkov et al. |
| 2006/0063995 A1 | 3/2006 | Yodh et al. |
| 2007/0020181 A1 | 1/2007 | Workman et al. |

(Continued)

FOREIGN PATENT DOCUMENTS

| | | |
|---|---|---|
| JP | 2005-300996 A | 10/2005 |
| JP | 2007-305193 A | 11/2007 |

*Primary Examiner* — Devin B Henson
*Assistant Examiner* — Joseph A Tombers
(74) *Attorney, Agent, or Firm* — Sughrue Mion, PLLC

(57) ABSTRACT

A healthcare apparatus according to an embodiment includes: a plurality of light sources configured to emit light of different wavelengths onto an object; a light detector configured to measure an optical signal of each of the wavelengths by receiving light reflected or scattered from the object; and a processor configured to obtain a blood glucose level and a blood flow index by using the optical signal of each of the wavelengths, and to estimate at least one from among dietary information and dietary metabolism state information by monitoring a blood glucose level change and a blood flow index change after ingestion of a food.

21 Claims, 12 Drawing Sheets

(56) References Cited

U.S. PATENT DOCUMENTS

| | | |
|---|---|---|
| 2008/0200781 A1 | 8/2008 | Van Herpen et al. |
| 2010/0075353 A1* | 3/2010 | Heaton ................. G16H 20/60 435/14 |
| 2010/0324432 A1 | 12/2010 | Björling et al. |
| 2015/0148636 A1 | 5/2015 | Benaron |
| 2016/0206816 A1 | 7/2016 | Pile-Spellman et al. |
| 2017/0049332 A1 | 2/2017 | Park et al. |
| 2017/0164878 A1* | 6/2017 | Connor ................. G09B 19/00 |
| 2017/0209083 A1 | 7/2017 | Zarandi et al. |

* cited by examiner

HEALTHCARE APPARATUS AND OPERATING METHOD THEREOF

CROSS-REFERENCE TO RELATED APPLICATION(S)

This application claims priority from Korean Patent Application No. 10-2017-0164566, filed on Dec. 1, 2017, in the Korean Intellectual Property Office, the entire disclosure of which is incorporated herein by reference for all purposes.

BACKGROUND

1. Field

One or more exemplary embodiments relate to a healthcare apparatus and an operating method thereof.

2. Description of the Related Art

A glycemic response in the human body varies depending on foods. Even if an equal amount of foods is consumed, foods are digested and absorbed at different speeds. In order to reflect various speeds of absorption of carbohydrates, a glycemic index (GI) has been developed. The GI is a number that indicates carbohydrate quality by reflecting the speed of postprandial absorption of glucose, and is a relative value that is determined by measuring a change in the blood glucose level two hours after ingestion of 50 g of carbohydrate in each food item with respect to a value of 100 which represents a blood glucose level after ingestion of a reference food product or 50 g of glucose.

However, the GI has limitations in that the figure may not reflect a person's characteristics (e.g., a degree of response to insulin, a degree of stress, etc.), or may not reflect actual dietary life of mainly eating a complex diet rather than a single food.

SUMMARY

One or more exemplary embodiment provide a healthcare apparatus and an operating method thereof, which may estimate dietary information or dietary metabolism state information by using a blood glucose level and a blood flow index.

In an aspect of an exemplary embodiment, there is provided a healthcare apparatus including: a plurality of light sources configured to emit light of different wavelengths onto an object; a light detector configured to measure an optical signal of each of the wavelengths by receiving light reflected or scattered from the object; and a processor configured to obtain a blood glucose level and a blood flow index by using the optical signal of each of the wavelengths, and to estimate at least one from among dietary information and dietary metabolism state information by monitoring a blood glucose level change and a blood flow index change after ingestion of a food by the object.

The processor may extract representative waveforms of each of the wavelengths from the optical signal of each of the wavelengths, may generate an integrated representative waveform by integrating the representative waveforms of each of the wavelengths, and may obtain the blood glucose level and the blood flow index by analyzing the integrated representative waveform.

The processor may segment the optical signal of each of the wavelengths into periods to generate a plurality of segmented signals, may obtain a similarity between the plurality of segmented signals of each of the wavelengths, and may extract the representative waveforms of each of the wavelengths based on the similarity.

The processor may generate the integrated representative waveform by subtracting or dividing a representative waveform of one wavelength from or by a representative waveform of another wavelength.

The processor may extract a feature from the integrated representative waveform, and may obtain the blood glucose level and the blood flow index based on the extracted feature.

The processor may use a blood glucose level calculation model, which defines a relationship between the feature and the blood glucose level, and a blood flow index calculation model which defines a relationship between the feature and the blood flow index.

The processor may compare the blood glucose level change and the blood flow index change after ingestion of the food with a pre-stored blood glucose level change and a pre-stored blood flow index change, respectively, and may estimate at least one from among the dietary information and the dietary metabolism state information based on the comparison.

When compared with the pre-stored blood glucose level change and the pre-stored blood flow index change, in response to at least one of a range of a blood glucose level variation and a range of a blood flow index variation being increased by a value equal to or higher than a first threshold value, and a time interval between a peak blood glucose level and a peak blood flow index being changed by a value lower than a second threshold value, the processor may estimate that the ingested food has higher carbohydrate.

When compared with the pre-stored blood glucose level change and the pre-stored blood flow index change, in response to a range of a blood glucose level variation and a range of a blood flow index variation being changed by a value lower than a third threshold value, and a time interval between a peak blood glucose level and a peak blood flow index being increased by a value equal to or higher than a fourth threshold value, the processor may estimate that the ingested food has higher fat.

When compared with the pre-stored blood glucose change and the pre-stored blood flow index change, in response to at least one of a range of a blood glucose level variation and a range of a blood flow index variation being increased, or a time interval between a peak blood glucose level and a peak blood flow index being increased, the processor may estimate that the dietary metabolism state of the object is not positive.

When compared with the pre-stored blood glucose change and pre-stored blood flow index change, in response to at least one of a range of a blood glucose level variation and a range of a blood flow index variation being decreased, or a time interval between a peak blood glucose level and a peak blood flow index being decreased, the processor may estimate that the dietary metabolism state of the object is positive.

The healthcare apparatus may further include a valid signal extractor including an acceleration sensor and configured to extract a valid signal from the measured optical signal.

The valid signal extractor may extract, as a valid signal, an optical signal which is measured when a value of the acceleration sensor does not exceed a threshold value, or an optical signal, of which the amplitude variation range is within a threshold range.

The healthcare apparatus may further include a preprocessor configured to remove a noise from the measured optical signal.

In an aspect of another exemplary embodiment, there is provided an operating method of a healthcare apparatus, the method including: emitting light of different wavelengths onto an object; measuring an optical signal of each of the wavelengths by receiving light reflected or scattered from the object; obtaining a blood glucose level and a blood flow index by using the optical signal of each of the wavelengths; and estimating dietary information or dietary metabolism state information by monitoring a blood glucose level change and a blood flow index change after ingestion of a food by the object.

The obtaining the blood glucose level and the blood flow index may include: extracting representative waveforms of each of the wavelengths from the optical signal of each of the wavelengths; generating an integrated representative waveform by integrating the representative waveforms of each of the wavelengths; and obtaining the blood glucose level and the blood flow index by analyzing the integrated representative waveform.

The extracting of the representative waveforms of each of the wavelengths may include: segmenting the optical signal of each of the wavelengths into periods to generate a plurality of segmented signals; obtaining a similarity between the plurality of segmented signals of each of the wavelengths; and extracting the representative waveforms of each of the wavelengths based on the similarity.

The generating of the integrated representative waveform may include generating the integrated representative waveform by subtracting or dividing a representative waveform of one wavelength from or by a representative waveform of another wavelength.

The obtaining the blood glucose level and the blood flow index may include: extracting a feature from the integrated representative waveform; and obtaining the blood glucose level and the blood flow index based on the extracted feature.

The estimating of at least one from among the dietary information and the dietary metabolism state information may include: comparing the blood glucose level change and the blood flow index change after ingestion of the food with a pre-stored blood glucose level change and a pre-stored blood flow index change; and estimating at least one from among the dietary information and the dietary metabolism state information based on the comparison.

The estimating of the at least one from among the dietary information and the dietary metabolism state information may include: when compared with the pre-stored blood glucose level change and the pre-stored blood flow index change, in response to at least one of a range of a blood glucose level variation and a range of a blood flow index variation being increased by a value equal to or higher than a first threshold value, and a time interval between a peak blood glucose level and a peak blood flow index being changed by a value lower than a second threshold value, estimating that the ingested food has higher carbohydrate; and when compared with the pre-stored blood glucose level change and the pre-stored blood flow index change, in response to a range of a blood glucose level variation and a range of a blood flow index variation being changed by a value lower than a third threshold value, and a time interval between a peak blood glucose level and a peak blood flow index being increased by a value equal to or higher than a fourth threshold value, the processor estimating that the ingested food has higher fat.

The estimating of the at least one from among the dietary information and the dietary metabolism state information may include: when compared with the pre-stored blood glucose change and the pre-stored blood flow index change, in response to at least one of a range of a blood glucose level variation and a range of a blood flow index variation being increased, or a time interval between a peak blood glucose level and a peak blood flow index being increased, estimating that the dietary metabolism state of the object is not positive; and when compared with the pre-stored blood glucose change and the pre-stored blood flow index change, in response to at least one of a range of a blood glucose level variation and a range of a blood flow index variation being decreased, or a time interval between a peak blood glucose level and a peak blood flow index being decreased, estimating that the dietary metabolism state of the object is positive.

BRIEF DESCRIPTION OF THE DRAWINGS

These and/or other aspects of the disclosure will become apparent and more readily appreciated from the following description of the exemplary embodiments, taken in conjunction with the accompanying drawings.

DETAILED DESCRIPTION

Figure 1:
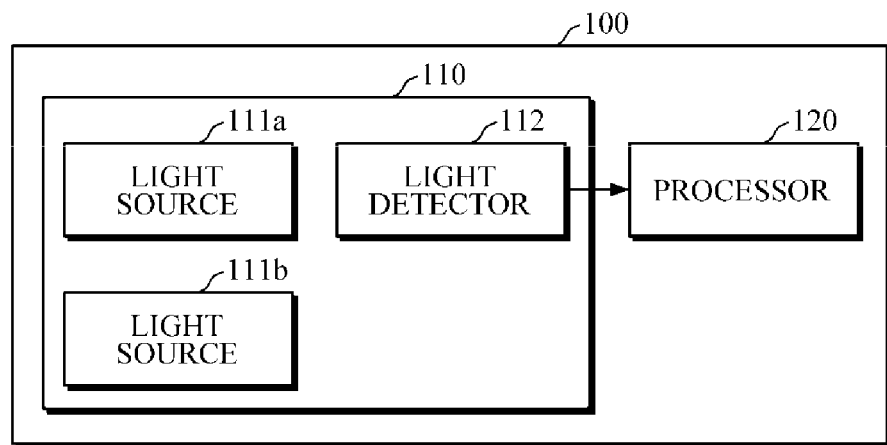
FIG. 1 is a block diagram illustrating an example of a healthcare apparatus.

Hereinafter, embodiments of the disclosure will be described in detail with reference to the accompanying drawings. It should be noted that, in the drawings, the same reference symbols refer to same parts although illustrated in other drawings. Throughout the drawings and the detailed description, unless otherwise described, the same drawing reference numerals will be understood to refer to the same elements, features, and structures. The relative size and depiction of these elements may be exaggerated for clarity, illustration, and convenience. In the following description, a detailed description of known functions and configurations incorporated herein will be omitted when it may obscure the subject matter of the disclosure.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to exemplary embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Further, components that will be described in the specification are discriminated merely according to functions mainly performed by the components. That is, two or more components which will be described later can be integrated into a single component. Furthermore, a single component which will be explained later can be separated into two or more components. Moreover, each component which will be described can additionally perform some or all of a function executed by another component in addition to the main function thereof. Some or all of the main function of each component which will be explained can be carried out by another component. Each component may be implemented as hardware, software, or a combination of both.

FIG. 1 is a block diagram illustrating an example of a healthcare apparatus according to an exemplary embodiment.

A healthcare apparatus 100 of FIG. 1 may be implemented as a software module or manufactured in the form of a hardware chip to be embedded in various types of electronic apparatuses. In this case, examples of the electronic apparatuses may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a watch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 1, the healthcare apparatus 100 includes an optical sensor 110 and a processor 120.

The optical sensor 110 may emit light of a specific wavelength onto an object, and may measure an optical signal by receiving light reflected or scattered from the object. In this case, the optical signal may be a photoplethysmogram (PPG) signal, which is merely exemplary and the optical signal is not limited thereto. To this end, the optical sensor 110 may include a plurality of light sources 111a and 111b, and a light detector 112.

Each of the light sources 111a and 111b may emit light of different wavelengths onto an object. For example, each of the light sources 111a and 111b may emit near infrared ray (NIR) or visible ray onto the skin of the object. However, a wavelength of light to be emitted by each of the light sources 111a and 111b may vary depending on the purpose of measurement or the types of components to be measured. In the embodiment, each of the light sources 111a and 111b may be a light emitting diode (LED), a laser diode, and the like, but this is merely exemplary and the light sources 111a and 111b are not limited thereto.

The light detector 112 may receive light, which is reflected or scattered from the object after being emitted by each of the light sources 111a and 111b, and may measure an optical signal of each wavelength. In the embodiment, the light detector 112 may be a photodiode, a photo transistor (PTr), a charge-coupled device (CCD), or the like. However, this is merely exemplary, and the light detector 112 is not necessarily required to be configured as a single element, but may be an array having a plurality of elements.

In addition, the optical sensor 110 may further include at least one optical element (e.g., mirror, etc.) which directs light, emitted by each of the light sources 111a and 111b, to a desired position of the object, and/or at least one optical element (e.g., mirror, etc.) which directs light, reflected or scattered from the object, to the light detector 112.

The processor 120 may control the overall operation of the healthcare apparatus 100. The processor 120 may include, for example, a microprocessor, a central processing unit (CPU), or an integrated circuit for executing programmable instructions.

The processor 120 may control the optical sensor 110 according to a user's request. In this case, the processor 120 may control turning on/off of each of the light sources by time-dividing the light sources. The processor 120 may drive each of the light sources based on driving conditions such as a current intensity, a pulse duration, and the like of each of the light sources. However, the processor 120 is not limited thereto, and may turn on the plurality of light sources all together so that the light sources may emit light at the same time.

The processor 120 may calculate a blood glucose level and a blood flow index by using the optical signal of each wavelength, and may estimate dietary information or dietary metabolism state information based on the calculated blood glucose level and blood flow index. Here, the blood flow index may indicate a blood flow, a variation in the blood flow, or a blood flow velocity. Further, the dietary information may include information related to the types of ingested food (e.g., carbohydrate-rich meal or food, fat-rich meal or food, etc.), and the dietary metabolism state information may include information on whether a dietary metabolism state is good or bad.

Although FIG. 1 illustrates two light sources 111a and 111b, this is merely for convenience of explanation, and not intended to be limiting.

Hereinafter, the processor 120 will be described in further detail with reference to FIGS. 2 to 4B.

Figure 2:
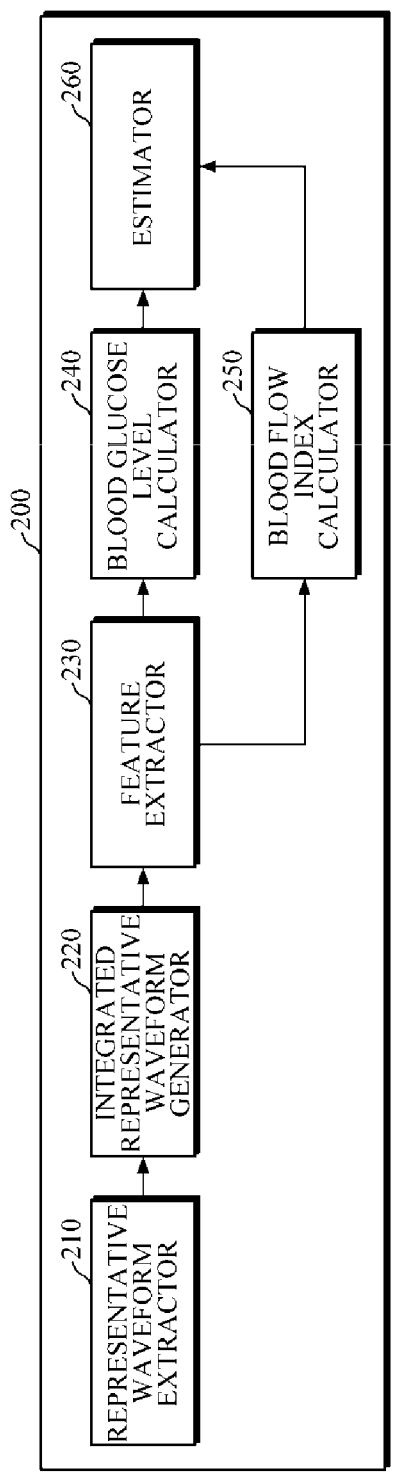
FIG. 2 is a block diagram illustrating an example of a processor.
Figure 3:
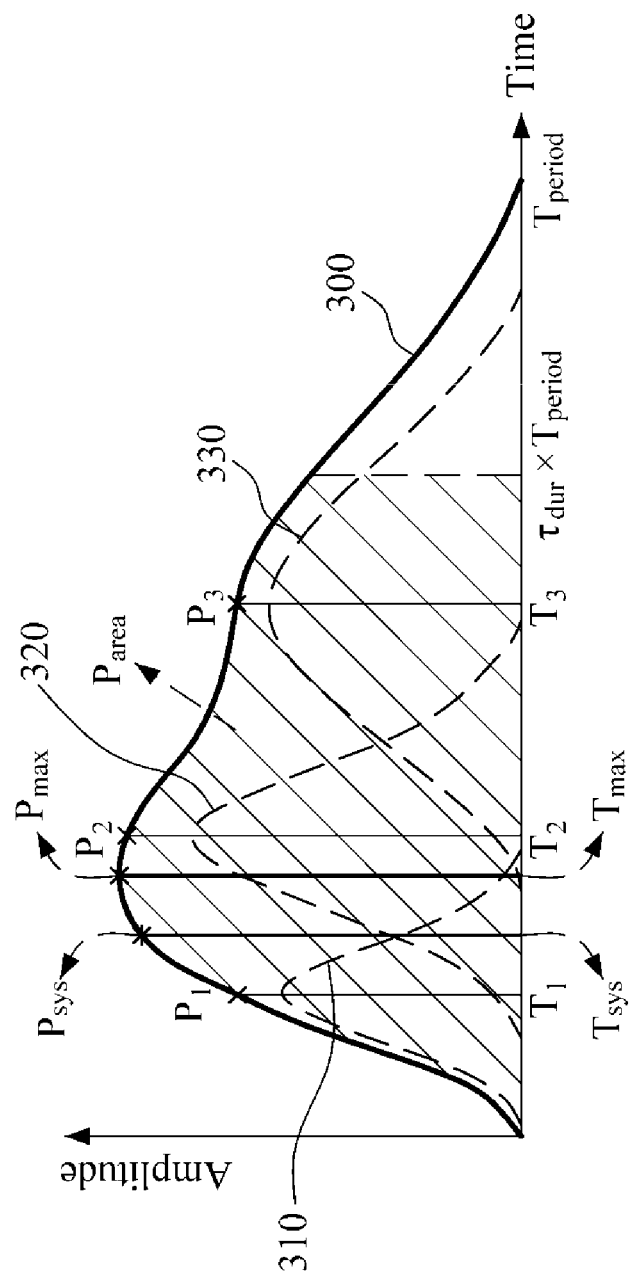
FIG. 3 is an exemplary diagram explaining features of an optical signal.
Figure 4A:
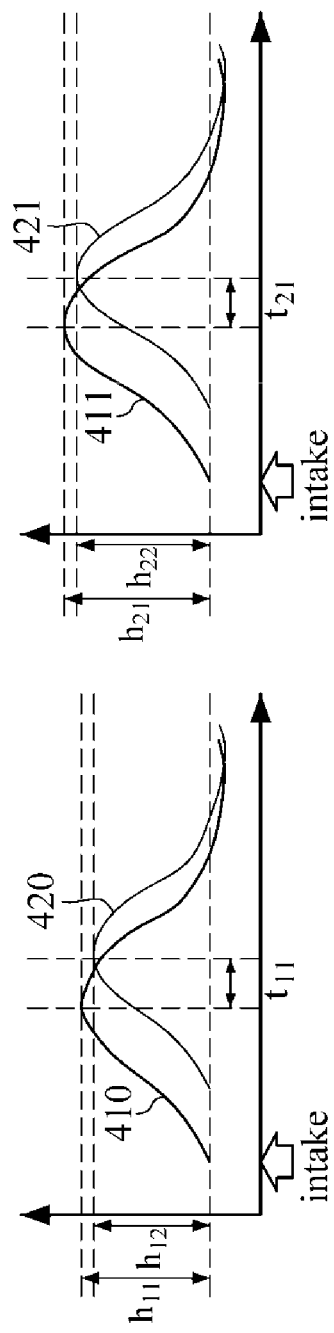
FIGS. 4A and 4B are exemplary diagrams explaining an example of estimating dietary information.
Figure 4B:
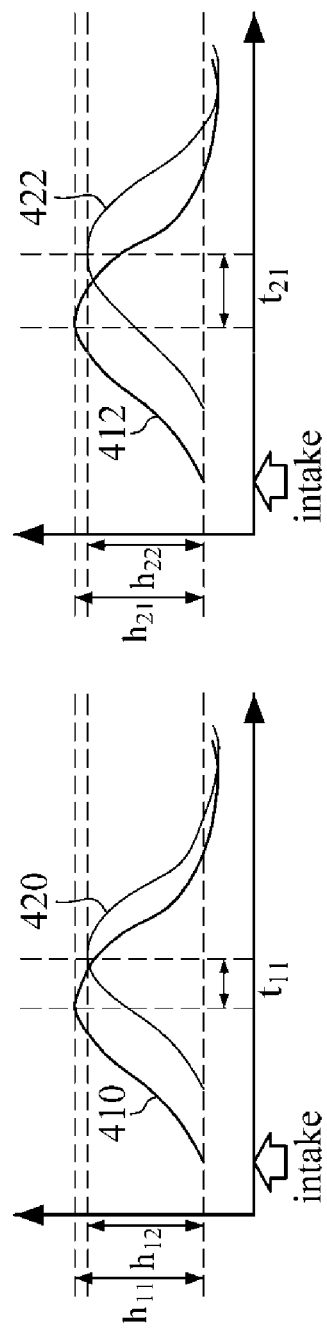

FIG. 2 is a block diagram illustrating an example of a processor; FIG. 3 is an exemplary diagram explaining features of an optical signal; and FIGS. 4A and 4B are exemplary diagrams explaining an example of estimating dietary information. A processor 200 of FIG. 2 may be an example of the processor 120 of FIG. 1.

Referring to FIG. 2, the processor 200 includes a representative waveform extractor 210, an integrated representative waveform generator 220, a feature extractor 230, a blood glucose level calculator 240, a blood flow index calculator 250, and an estimator 260.

The representative waveform extractor 210 may extract a representative waveform of each wavelength from an optical signal of each wavelength. Here, the representative waveform may indicate a signal that may best represent features of an optical signal of each wavelength. In one embodiment, the representative waveform extractor 210 may segment an optical signal of each wavelength into periods, to generate a plurality of segmented signals, and may extract a segmented signal, having the highest similarity between the plurality of segmented signals, as a representative waveform of the wavelength. The representative waveform extractor 210 may use a similarity calculation algorithm, such as Euclidean distance, Manhattan Distance, Cosine Distance, Mahalanobis Distance, Jaccard Coefficient, Extended Jaccard Coefficient, Pearson's Correlation Coefficient, Spearman's Correlation Coefficient, and the like.

The integrated representative waveform generator 220 may generate an integrated representative waveform by integrating representative waveforms of each wavelength. In one embodiment, the integrated representative waveform generator 220 may generate the integrated representative waveform by subtracting or dividing a representative waveform of one wavelength from or by a representative waveform of another wavelength. In this manner, the processor 120 may remove an effect by factors, other than glucose, among the factors affecting the blood flow.

The feature extractor 230 may extract features, which are dependent on a change in the blood glucose level and/or the blood flow index, from the generated integrated representative waveform.

Hereinafter, the features will be described in further detail with reference to FIG. 3. FIG. 3 is a diagram illustrating a PPG signal as an optical signal.

Referring to FIG. 3, a waveform of a PPG signal 300 may be generated by superimposing a propagation wave 310, which progresses from the heart to the distal end of the body, and reflection waves 320 and 330 which return from the distal end of the body. That is, the PPG signal 300 may be formed with three or more component pulses 310 to 330 which are superimposed on each other. Here, the reference numeral 300 denotes a PPG signal of a period Tperiod, the reference numeral 310 denotes a first component pulse, the reference 320 denotes a second component pulse, and the reference numeral 330 denotes a third component pulse. Further, T1 denotes a time at a peak value point of the first component pulse 310, P1 is an amplitude of the PPG signal 300 at T1, T2 denotes a time at a peak value point of the second component pulse 320, P2 denotes an amplitude of the PPG signal 300 at T2, T3 denotes a time at a peak value point of the third component pulse 330, and P3 denotes an amplitude of the PPG signal 300 at T3. In addition, $T_{max}$ denotes a time at a peak value point of the PPG signal 300, $P_{max}$ denotes an amplitude of the PPG signal 300 at $T_{max}$, $T_{sys}$ denotes a time at a midpoint between T1 and $T_{max}$, $P_{sys}$ denotes an amplitude of the PPG signal 300 at $T_{sys}$, $\tau_{dur}$ denotes a configuration factor ($0 \leq \tau_{dur} \leq 1$, e.g., 0.7) of a system, and $P_{area}$ denotes a sum of amplitudes of the PPG signal 300 from 0 to $T_{dur} \times T_{period}$ (second section).

In one embodiment, the features may include any one of $P_{max}$, $P_1$, $P_2$, $P_3$, $P_{sys}$, $P_{area}$, $T_{max}$, $T_1$, $T_2$, $T_3$, and $T_{sys}$, and linear or non-linear combinations thereof. However, this is merely exemplary and is not intended to be limiting. Further, in FIG. 3, $T_{sys}$ denotes a time at a midpoint between $T_1$ and $T_{max}$, but is not limited thereto. That is, $T_{sys}$ may be any one internally dividing point between $T_1$ and $T_{max}$, and may be any one internally dividing point between $T_1$ and $T_2$.

That is, the feature extractor 230 may extract, as features, any one of $P_{max}$, $P_1$, $P_2$, $P_3$, $P_{sys}$, $P_{area}$, $T_{max}$, $T_1$, $T_2$, $T_3$, and $T_{sys}$, and linear or non-linear combinations thereof from the generated integrated representative waveform.

The blood glucose level calculator 240 may calculate a blood glucose level analyzing the extracted features. In one embodiment, the blood glucose level calculator 240 may calculate a blood glucose level by using a predetermined blood glucose level calculation model. In this case, the blood glucose level calculation model defines a relationship between features and blood glucose levels, and may be pre-generated by using various model building methods (e.g., machine learning, regression analysis, etc.) to be pre-stored in an internal or external database of the processor 200.

The blood flow index calculator 250 may calculate a blood flow index by analyzing the extracted features. In one embodiment, the blood flow index calculator 250 may calculate a blood flow index by using a predetermined blood flow index calculation model. In this case, the blood flow index calculation model defines a relationship between the features and the blood flow index, and may be pre-generated by using various model building methods (e.g., machine learning, regression analysis, etc.) to be pre-stored in an internal or external database of the processor 200.

The estimator 260 may monitor a change in a blood glucose level and a blood flow index for a predetermined period of time after ingestion of a food based on the calculated blood glucose level and blood flow index, and may estimate dietary information and dietary metabolism state information by analyzing the monitoring result.

The estimator 260 may estimate dietary information of the ingested food by comparing the change in a blood glucose level and a blood flow index, which is monitored for a predetermined period of time after ingestion of a food, with a pre-stored change in a blood glucose level and a blood flow index. In this case, the pre-stored change in the blood glucose level and the blood flow index may be obtained by monitoring an object for a predetermined period of time after ingestion of a reference food by the object by using the healthcare apparatus 100, and may be pre-stored in an internal or external database.

For example, upon monitoring the change in a blood glucose level and a blood flow index for a predetermined period of time after ingestion of a food, when compared with the pre-stored blood glucose level change and the pre-stored blood flow index change, when a range of a blood glucose level variation and/or a range of a blood flow index variation is increased by a value equal to or higher than a first threshold value, and a time interval between a peak blood glucose level and a peak blood flow index is changed by a value lower than a second threshold value, the estimator 260 may estimate that the ingested food is a carbohydrate-rich food (or food having higher carbohydrate). Further, upon monitoring the change in a blood glucose level and a blood flow index for a predetermined period of time after ingestion of a food, when compared with the pre-stored blood glucose level change and the pre-stored blood flow index change, when a range of a blood glucose level variation and/or a range of a blood flow index variation is changed by a value lower than a third threshold value, whereas a time interval between a peak blood glucose level and a peak blood flow index is increased by a value equal to or higher than a fourth threshold value, the estimator 260 may estimate that the ingested food is a fat-rich food (or food having higher fat).

Hereinafter, with reference to FIGS. 4A and 4B, the estimation of dietary information will be described in further detail. In FIGS. 4A and 4B, a reference numeral 410 denotes the pre-stored change in the blood glucose level, and a reference numeral 420 denotes the pre-stored change in the blood flow index. In this case, the pre-stored blood glucose level change 410 and the pre-stored blood flow index change 420 are information measured by monitoring the object for a predetermined period of time after ingestion of the reference food, and may be pre-stored in an internal or external database.

Referring to FIG. 4A, the estimator 260 may monitor a blood glucose level change 411 and a blood flow index change 421 after the ingestion of a food, based on the blood glucose level and the blood flow index which are calculated by the blood flow index calculator 250. Further, the estimator 260 may compare the blood glucose level change 411 and the blood flow index change 421 with the pre-stored blood glucose level change 410 and the pre-stored blood flow index change 420. In the case of Ha 4A, a range $h_{21}$ of a blood glucose level variation after the ingestion of a food is increased by a value equal to or higher than the first threshold value when compared with a range $h_{11}$ of a blood glucose level variation, and a range $h_{22}$ of a blood flow index variation after the ingestion of a food is increased by a value equal to or higher than the first threshold value when compared with a range $h_{12}$ of a blood flow index variation whereas a difference between a time interval $t_{21}$ between the peak blood glucose level and the peak blood flow index after the ingestion of a food and a time interval $t_{11}$ between the peak blood glucose level and the peak blood flow index is lower than the predetermined second threshold value. In this case, the estimator 260 may estimate the ingested food as a carbohydrate-rich food.

Referring to FIG. 4B, the estimator 260 may monitor a blood glucose level change 412 and a blood flow index change 422 after the ingestion of a food, based on the blood glucose level and the blood flow index which are calculated by the blood flow index calculator 250. Further, the estimator 260 may compare the blood glucose level change 412 and the blood flow index change 422 after the ingestion of a food with the pre-stored blood glucose level change 410 and the pre-stored blood flow index change 420. In the case of FIG. 4B, a difference between the range $h_{21}$ of a blood glucose level variation after the ingestion of a food and the range of a blood glucose level variation lower threshold value, and a difference between the range $h_{22}$ of a blood flow index variation after the ingestion of a food and the range $11_{12}$ of a blood flow index variation is Lower than the third threshold value; whereas the time interval $t_{21}$ between the peak blood glucose level and the peak blood flow index after the ingestion of a food is increased by a value equal to or higher than the fourth threshold value when compared with the interval $t_{11}$ between the peak blood glucose level and the peak blood flow index. In this case, the estimator 260 may estimate the ingested food as a fat-rich food.

Referring back to FIG. 2, the estimator 260 may estimate metabolism state information by comparing the blood glucose level change and the blood flow index change, which are monitored for a predetermined period of time after the ingestion of a food, with the pre-stored blood glucose level change and the blood flow index change. It is assumed that the currently ingested food is the sa reference food. That is, in the case where the object ingests the reference food, the estimator 260 may monitor a blood glucose level change and a blood flow index change for a predetermined period of time after the ingestion of the reference food, and may estimate whether the dietary metabolism state of the object is good (or positive) or bad (or not positive) by comparing the monitored blood glucose level change and blood flow index change with the pre-stored blood glucose level change and the pre-stored blood flow index change.

For example, the estimator 260 may monitor the blood glucose level change and the blood flow index change for a predetermined period of time after the object ingests the reference food, and may compare the monitored blood glucose level change and blood flow index change with the pre-stored blood glucose change and the pre-stored blood flow index change. When compared with the pre-stored blood glucose change and the pre-stored blood flow index change, when a range of a blood glucose level variation and/or a range of a blood flow index variation is increased, or when a time interval between the peak blood glucose level and the peak blood flow index is increased, the estimator 260 may estimate that the dietary metabolism state is bad; and when the range of a blood glucose level variation and/or the range of a blood flow index variation is decreased, or the time interval between the peak blood glucose level and the peak blood flow index is decreased, the estimator 260 may estimate that the dietary metabolism state is good.

Figure 5:
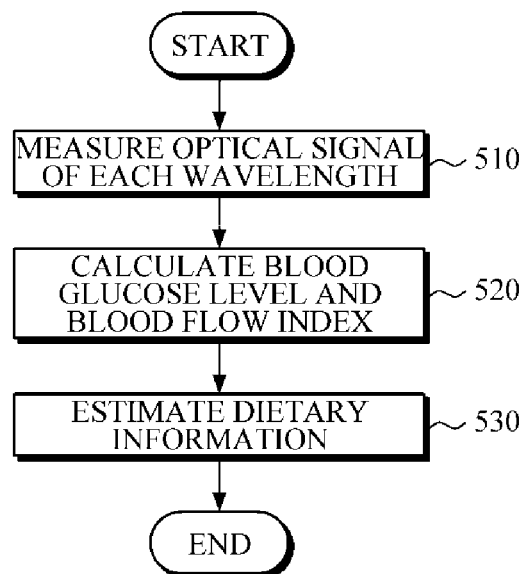
FIG. 5 is a flowchart illustrating an example of an operating method of a healthcare apparatus.

FIG. 5 is a flowchart illustrating an example of an operating method of a healthcare apparatus. The operating method of the healthcare apparatus of FIG. 5 may be performed by the healthcare apparatus 100 of FIG. 1.

Referring to FIGS. 1 and 5, the healthcare apparatus 100 may unit light of different wavelengths onto an object, and may measure an optical signal of each wavelength by receiving light reflected or scattered from the object in 510.

The healthcare apparatus 100 may calculate a blood glucose level and a blood flow index by using the optical signal of each wavelength in 520.

The healthcare apparatus 100 may monitor a blood glucose level change and a blood flow index change after the ingestion of a food based on the calculated blood glucose level and blood flow index, and may estimate dietary information based on the monitoring result in 530. In one embodiment, the healthcare apparatus 100 may estimate dietary information of the ingested food by comparing the blood glucose level change and blood flow index change, which are monitored for a predetermined period of time after the ingestion of a food, with the pre-stored blood glucose level change and the pre-stored blood flow index change. For example, upon monitoring, when compared with the pre-stored change in the blood glucose level and the blood flow index, when the range of a blood glucose level variation and/or the range of a blood flow index variation by a value equal to or higher than the first threshold value, and based on the time interval between the peak blood glucose level and the peak blood flow index being changed by a value lower than the second threshold value, the healthcare apparatus 100 may estimate that the ingested food is a carbohydrate-rich food. Further, upon monitoring, when compared with the pre-stored change in the blood glucose level and the blood flow index, when the range of a blood glucose variation and/or the range of a blood flow index variation is changed by a value lower than the third threshold value, whereas the time interval between the peak blood glucose level and the peak blood flow index is increased by a value equal to or higher than the fourth threshold value, the healthcare apparatus 100 may estimate that the ingested food is a fat-rich food.

Figure 6:
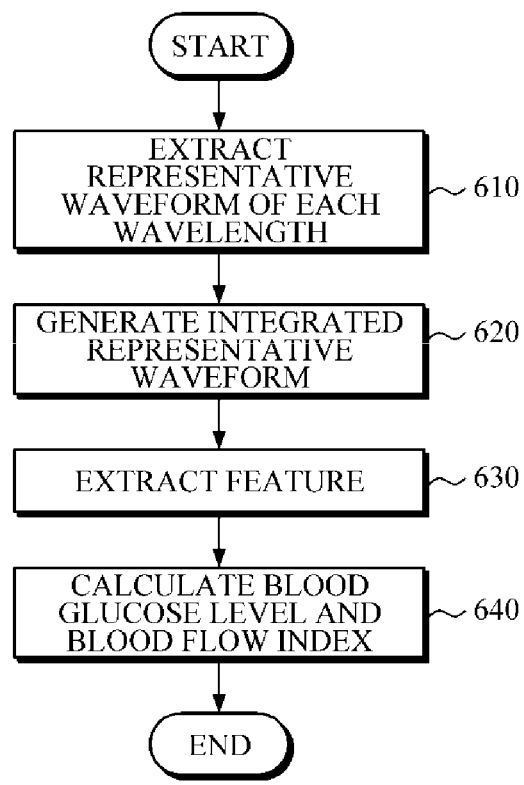
FIG. 6 is a flowchart illustrating an example of calculating a blood glucose level and a blood flow index.

FIG. 6 is a flowchart illustrating an example of calculating a blood glucose level and a blood flow index. The calculating of the blood glucose level and the blood flow index of FIG. 6 may be an example of calculating the blood glucose level and the blood flow index in 520 of FIG. 5.

Referring to FIGS. 1 and 6, the healthcare apparatus 100 may extract a representative waveform of each wavelength from the optical signal of each wavelength in 610. For example, the healthcare apparatus 100 may segment an optical signal of each wavelength into periods, to generate a plurality of segmented signals, and may extract a segmented signal, having the highest similarity between the plurality of segmented signals, as a representative waveform of the wavelength.

The healthcare apparatus 100 may generate an integrated representative waveform by integrating representative waveforms of each wavelength in 620. For example, the integrated representative waveform generator 220 may generate the integrated representative waveform by subtracting or dividing a representative waveform of one wavelength from or by a representative waveform of another wavelength.

The healthcare apparatus 100 may extract features, which are dependent on a change in the blood glucose level and/or the blood flow index, from the generated integrated representative waveform in 630. The features are described above in detail with reference to FIG. 3, such that detailed description thereof will be omitted.

The healthcare apparatus 100 may calculate a blood glucose level and a blood flow index by analyzing the extracted features in 640. In one embodiment, the healthcare apparatus 100 may calculate the blood glucose level by using a blood glucose level calculation model or a blood flow index calculation model.

Figure 7:
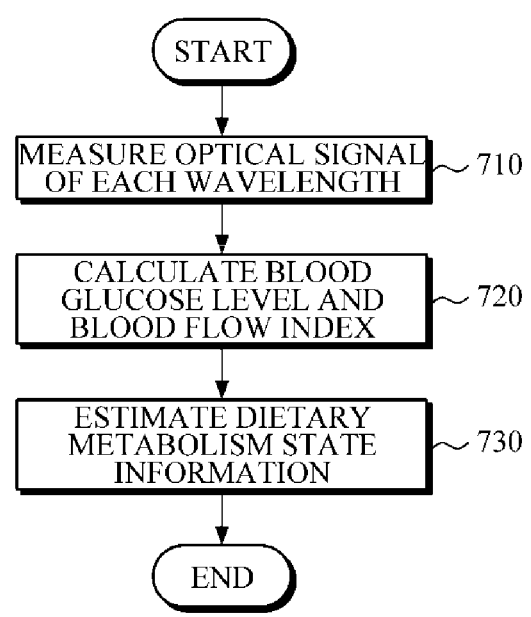
FIG. 7 is a flowchart illustrating another example of an operating method of a healthcare apparatus.

FIG. 7 is a flowchart illustrating another example of an operating method of a healthcare apparatus. The operating method of FIG. 7 may be performed by the healthcare apparatus 100 of FIG. 1.

Referring to FIGS. 1 and 7, the healthcare apparatus 100 may emit light of different wavelengths onto an object, and may measure an optical signal of each wavelength by receiving light reflected or scattered from the object in 710.

The healthcare apparatus 100 may calculate a blood glucose level and a blood flow index by using the optical signal of each wavelength in 720. For example, the healthcare apparatus 100 may extract a representative waveform of each wavelength from the optical signal of each wavelength, may generate an integrated representative waveform by integrating representative waveforms of each wavelength, may extract features from the generated integrated representative waveform, and may calculate a blood glucose level and a blood flow index by analyzing the extracted features.

The healthcare apparatus 100 may estimate dietary metabolism state information by comparing the blood glucose level change and the blood flow index change, which are monitored for a predetermined period of time after the ingestion of the reference food, with the pre-stored blood glucose level change and blood flow index change in 730. For example, the healthcare apparatus 100 may monitor the blood glucose level change and the blood flow index change for a predetermined period of time after the object ingests the reference food, and may compare the monitored blood glucose level change and blood flow index change with the pre-stored blood glucose level change and blood flow index change. When compared with the pre-stored blood glucose level change and blood flow index change, when the range of a blood glucose level variation and/or the range of a blood flow index variation is increased, or when a time interval between the peak blood glucose level and the peak blood flow index is increased, the healthcare apparatus 100 may estimate that the dietary metabolism state is bad; and when the range of a blood glucose level variation and/or the range of a blood flow index variation is decreased, or the time interval between the peak blood glucose level and the peak blood flow index is decreased, the healthcare apparatus 100 may estimate that the dietary metabolism state is good.

Figure 8:
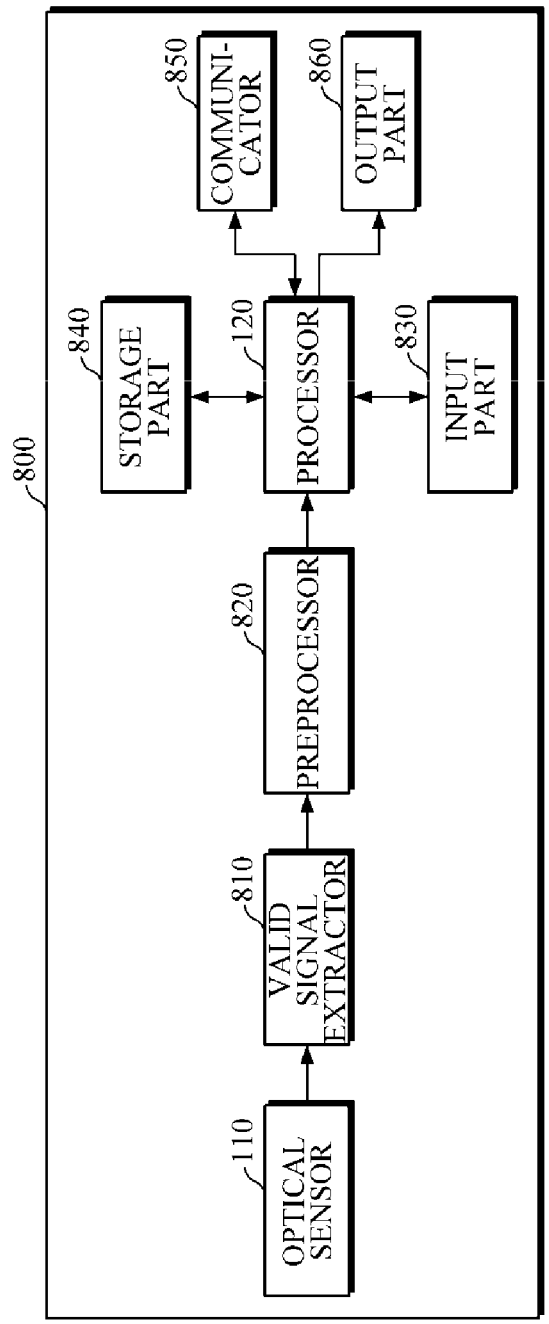
FIG. 8 is a block diagram illustrating another example of a healthcare apparatus.

FIG. 8 is a block diagram illustrating another example of a healthcare apparatus.

A healthcare apparatus 800 of FIG. 8 may be implemented as a software module or may be manufactured in the form of a hardware chip to be embedded in various types of electronic apparatuses. In this case, examples of the electronic apparatuses may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a watch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 8, the healthcare apparatus 800 includes an optical sensor 110, a valid signal extractor 810, a preprocessor 820, a processor 120, an input part 830, a storage part 840, a communicator 850, and an output part 860. Here, the optical sensor 110 and the processor 1 are described above with reference to FIGS. 1 to 7, such that repeated description will be omitted.

The valid signal extractor 810 may extract a valid signal from an optical signal measured by the optical sensor 110. In one embodiment, the valid signal extractor 810 may include an acceleration sensor and the like, and may extract an optical signal, which is measured when a value of the acceleration sensor does not exceed a threshold value, as a valid signal. In another embodiment, the valid signal extractor 810 may extract an optical signal, of which the amplitude variation is within a threshold range, as a valid signal.

The preprocessor 820 may remove a noise from the optical signal. For example, the preprocessor 820 may remove the noise from the optical signal by using various filtering methods, such as a low pass filter, moving average, and the like.

The input part 830 may receive input of various operation signals from a user. In one embodiment, the input part 330 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage part 840 may store programs or commands for operation of the healthcare apparatus 800, and may store data input to and output from the healthcare apparatus 800. Further, the storage part 840 may store the optical signal measured by the optical sensor 110, the blood glucose level calculation model, the blood flow index calculation model, the blood glucose level change and the blood flow index change which are monitored for a predetermined period of time after the ingestion of the reference food, the blood glucose level change and the blood flow index change which are monitored by the processor 120 for a predetermined period of time after the ingestion of a food, the dietary information and the dietary metabolism state information which are estimated by the processor 120, and the like. The storage part 840 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the healthcare apparatus 800 may operate an external storage medium, such as web storage and the like, which performs a storage function of the storage part 840 on the Internet.

The communicator 850 may perform communication with an external device. For example, the communicator 350 may transmit the input data, the stored data, the processed data, and the like of the healthcare apparatus 800 to the external device, or may receive, from the external device, various data useful for estimation of the dietary information and the dietary metabolism state information.

In this case, the external device may be medical equipment using the input data, the stored data, the processed data, and the like of the healthcare apparatus 800, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communicator 850 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3 G communication, 4 G communication, 5 G communication, and the like. However, this is merely exemplary and is not intended to be limiting.

The output part 860 may output the input data, the stored data, the processed data, and the like of the healthcare apparatus 800. In one embodiment, the output part 860 may output the input data, the stored data, the processed data, and the like of the healthcare apparatus 800 by using at least one of an acoustic method, a visual method, and a tactile method. To this end, the output part 860 may include a display, a speaker, a vibrator, and the like.

Figure 9:
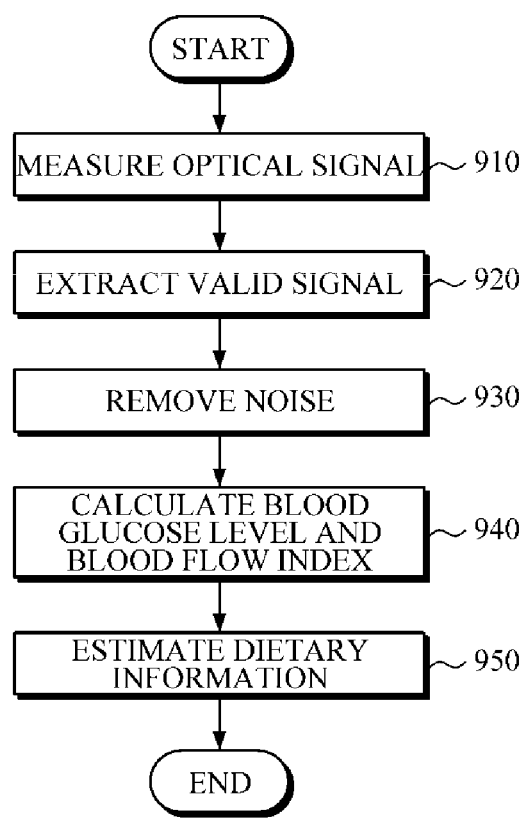
FIG. 9 is a flowchart illustrating an example of an operating method of a healthcare apparatus.

FIG. 9 is a flowchart illustrating an example of an operating method of a healthcare apparatus. The operating method of FIG. 9 may be performed by the healthcare apparatus 800 of FIG. 8.

Referring to FIGS. 8 and 9, the healthcare apparatus 800 may emit light t of different wavelengths onto an object, and may measure an optical signal of each wavelength by receiving light reflected or scattered from the object in 910.

The healthcare apparatus 800 may extract a valid signal from the measured optical signal in 920. For example, the healthcare apparatus 800 includes an acceleration sensor and the like, and may extract, as a valid signal, an optical sensor which is measured when a value of the acceleration sensor does not exceed a threshold value, or an optical signal, of which the amplitude variation range is within a threshold range.

The healthcare apparatus 800 may remove a noise from the optical signal in 930. For example, the healthcare apparatus 800 may remove the noise from the optical signal by using various filtering methods, such as a low pass filter, moving average, and the like.

The healthcare apparatus 800 may calculate a blood glucose level and a blood flow index of an object by using the optical signal of each wavelength in 940.

The healthcare apparatus 800 may monitor a blood glucose level change and a blood flow index change after the ingestion of a food based on the calculated blood glucose level and the blood flow index, and may estimate dietary information based on the monitoring result in 950.

Figure 10:
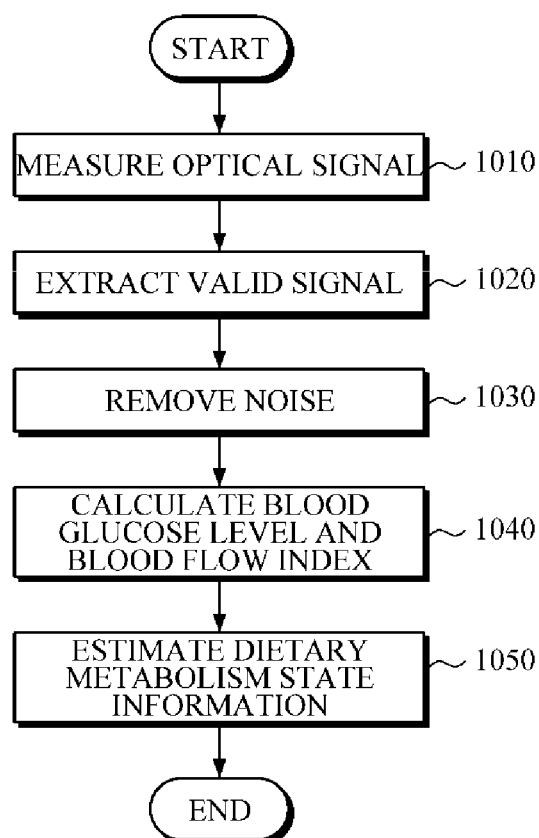
FIG. 10 is a flowchart illustrating another example of an operating method of a healthcare apparatus.

FIG. 10 is a flowchart illustrating another example of an operating method of a healthcare apparatus. The operating method of FIG. 10 may be performed by the healthcare apparatus 800.

Referring to FIGS. 8 and 10, the healthcare apparatus 800 may emit light of different wavelengths onto an object, and may measure an optical signal of each wavelength by receiving light reflected or scattered from the object in 1010.

The healthcare apparatus 800 may extract a valid signal from the measured optical signal in 1020. For example, the healthcare apparatus 800 includes an acceleration sensor and the like, and may extract, as a valid signal, an optical sensor which is measured when a value of the acceleration sensor does not exceed a threshold value, or may extract an optical signal, of which the amplitude variation range is within a threshold range, as a valid signal.

The healthcare apparatus 800 may remove a noise from the optical signal in 1030. For example, the healthcare apparatus 800 may remove the noise from the optical signal by using various filtering methods, such as a low pass filter, moving average, and the like.

The healthcare apparatus 800 may calculate a blood glucose level and a blood flow index of an object by using the optical signal of each wavelength in 1040.

The healthcare apparatus 800 may estimate dietary metabolism state information by comparing the blood glucose level change and the blood flow index change, which are monitored for a predetermined period of time after the ingestion of the reference food, with the pre-stored blood glucose level change the pre-stored and blood flow index change in 1050.

Figure 11:
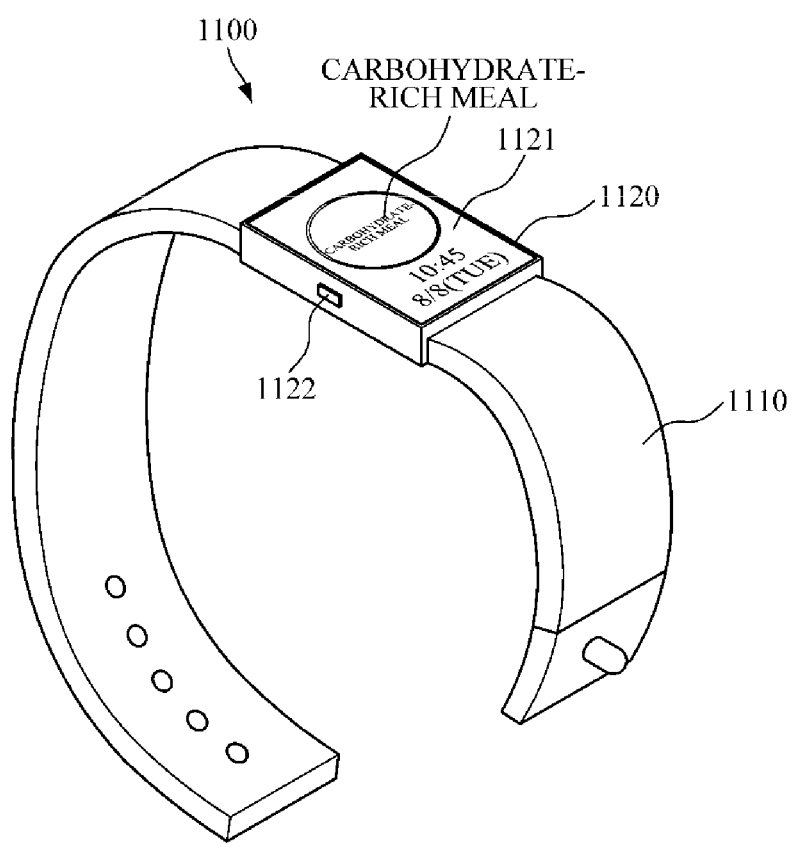
FIG. 11 is a diagram illustrating a wrist-type wearable device.

FIG. 11 is a diagram illustrating a wrist-type wearable device.

Referring to FIG. 11, a wrist-type wearable device 1100 includes a strap 1110 and a main body 1120.

The strap 1110 may be formed to be detachable from the main body 1120 and may be connected at both sides of the main body 1120 to be fastened to each other, or may be integrally formed as a smart band. The strap 1110 may be made of a flexible material to bend around a user's wrist so that the main body 1120 may be worn around a user's wrist.

The main body 1120 may include the above-described healthcare apparatuses 100 and 800. Further, the main body 1120 may include a battery which supplies power to the wrist-type wearable device 1100 and the healthcare apparatuses 100 and 800.

The optical sensor may be mounted at the bottom of the main body 1120 to be exposed to the wrist of a user. In this manner, when a user wears the wrist-type wearable device 1100, the light sensor may naturally come into contact with a user's skin.

The wrist-type wearable device 1100 may further include a display 1121 and an input part 1122 which are mounted in the main body 1120. The display 1121 may display data processed by the wrist-type wearable device 1100 and the healthcare apparatuses 100 and 800, processing result data, and the like thereof. The input part 1122 may receive input of various operation signals from a user.

The exemplary embodiments can be realized as a computer-readable code written on a computer-readable recording medium. The computer-readable recording medium may be any type of recording device in which data is stored in a computer-readable manner.

The disclosure can be realized as a computer-readable code written on a computer-readable recording medium. Codes and code segments needed for realizing the disclosure can be easily deduced by computer programmers of ordinary skill in the art. The computer-readable recording medium may be any type of recording device in which data is stored in a computer-readable manner. Examples of the computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

At least one of the components, elements, modules or units described herein may be embodied as various numbers of hardware, software and/or firmware structures that execute respective functions described above, according to an exemplary embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the above block diagrams, communication between the components, elements or units may be performed through the bus. Functional aspects of the above exemplary embodiments may be implemented in algorithms that execute on one or more processors. Furthermore, the components, elements or units represented by a block or processing operations may employ any number of related art techniques for electronics configuration, signal processing and/or control, data processing and the like.

The disclosure has been described herein with regard to exemplary embodiments. However, it will be obvious to those skilled in the art that various modifications can be made without departing from the gist of the invention. Therefore, it is to be understood that that the scope of the invention is not limited to the above-mentioned embodiments, but is intended to include various modifications and equivalents included within the spirit and scope of the appended claims.

What is claimed is:

1. A healthcare apparatus, comprising:
a plurality of light sources configured to emit light of different wavelengths onto an object;
a light detector configured to measure an optical signal of each of the wavelengths by receiving light reflected or scattered from the object; and
a processor configured to obtain a blood glucose level and a blood flow index by using the optical signal of each of the wavelengths, and to estimate at least one from among dietary information and dietary metabolism state information by monitoring a blood glucose level change and a blood flow index change after ingestion of a food by the object,
wherein the processor is further configured to compare the blood glucose level change after the ingestion of the food with a pre-stored blood glucose level change and compare the blood flow index change after the ingestion of the food with a pre-stored blood flow index change, and
wherein the processor is further configured to estimate the at least one from among the dietary information and the dietary metabolism state information, based on a time interval between a peak point of the blood glucose level and a peak point of the blood flow index being changed by a value lower than at least one threshold value according to a result of comparison of the blood glucose level change and the blood flow index change.

2. The apparatus of claim 1, wherein the processor is further configured to:
extract representative waveforms of each of the wavelengths from the optical signal of each of the wavelengths;
generate an integrated representative waveform by integrating the representative waveforms of each of the wavelengths; and
obtain the blood glucose level and the blood flow index based on the integrated representative waveform.

3. The apparatus of claim 2, wherein the processor is further configured to:
segment the optical signal of each of the wavelengths into periods to generate a plurality of segmented signals;
obtain a similarity between the plurality of segmented signals of each of the wavelengths; and
extract the representative waveforms of each of the wavelengths based on the similarity.

4. The apparatus of claim 2, wherein the processor is further configured to generate the integrated representative waveform by subtracting or dividing a representative waveform of one wavelength from or by a representative waveform of another wavelength.

5. The apparatus of claim 2, wherein the processor is further configured to extract a feature from the integrated representative waveform, and obtain the blood glucose level and the blood flow index based on the extracted feature.

6. The apparatus of claim 5, wherein the processor is further configured to obtain the blood glucose level and the blood flow index based on a blood glucose level calculation model, which defines a relationship between the feature and the blood glucose level, and a blood flow index calculation model which defines a relationship between the feature and the blood flow index.

7. The apparatus of claim 1, wherein when compared with the pre-stored blood glucose level change and the pre-stored blood flow index change, in response to at least one of a range of a blood glucose level variation and a range of a blood flow index variation being increased by a value equal to or higher than a first threshold value, and the time interval between the peak blood glucose level and the peak blood flow index being changed by the value lower than a second threshold value, the processor is further configured to estimate that the ingested food has higher carbohydrate.

8. The apparatus of claim 1, wherein when compared with the pre-stored blood glucose level change and the pre-stored blood flow index change, in response to a range of a blood glucose level variation and a range of a blood flow index variation being changed by a value lower than a third threshold value with respect to the pre-stored blood glucose level change and the pre-stored blood flow index change, and the time interval between the peak blood glucose level and the peak blood flow index being increased by a value equal to or higher than a fourth threshold value, the processor is further configured to estimate that the ingested food has higher fat.

9. The apparatus of claim 1, wherein when compared with the pre-stored blood glucose level change and the pre-stored blood flow index change, in response to at least one of a range of a blood glucose level variation and a range of a blood flow index variation being increased, or the time interval between the peak blood glucose level and the peak blood flow index being increased, the processor is further configured to estimate that dietary metabolism state of the object is not positive.

10. The apparatus of claim 1, wherein when compared with the pre-stored blood glucose level change and the pre-stored blood flow index change, in response to at least one of a range of a blood glucose level variation and a range of a blood flow index variation being decreased, or the time interval between the peak blood glucose level and the peak blood flow index being decreased, the processor is further configured to estimate that dietary metabolism state of the object is positive.

11. The apparatus of claim 1, further comprising a valid signal extractor comprising an acceleration sensor and configured to extract a valid signal from the measured optical signal.

12. The apparatus of claim 11, wherein the valid signal extractor is further configured to extract, as the valid signal, at least one from among an optical signal which is measured when a value of the acceleration sensor does not exceed a threshold value and an optical signal, of which an amplitude variation range is within a threshold range.

13. The apparatus of claim 1, further comprising a preprocessor configured to remove a noise from the measured optical signal.

14. The healthcare apparatus of claim 1, wherein the processor is further configured to determine that the greater the time interval between the peak point of the blood glucose level and the peak point of the blood flow index is, the worse a dietary metabolism state of the object is.

15. An operating method of a healthcare apparatus, the method comprising:
emitting light of different wavelengths onto an object;
measuring an optical signal of each of the wavelengths by receiving light reflected or scattered from the object;
obtaining a blood glucose level and a blood flow index by using the optical signal of each of the wavelengths; and
estimating at least one from among dietary information and dietary metabolism state information by monitoring a blood glucose level change and a blood flow index change after ingestion of a food by the object,
wherein the estimating comprises: comparing the blood glucose level change after the ingestion of the food with a pre-stored blood glucose level change and comparing the blood flow index change after the ingestion of the food with a pre-stored blood flow index change; and
estimating the at least one from among the dietary information and the dietary metabolism state information, based on a time interval between a peak point of the blood glucose level and a peak point of the blood flow index being changed by a value lower than at least one threshold value according to a result of a comparison of the blood glucose level change and the blood flow index change.

16. The method of claim 15, wherein the obtaining comprises:
extracting representative waveforms of each of the wavelengths from the optical signal of each of the wavelengths;
generating an integrated representative waveform by integrating the representative waveforms of each of the wavelengths; and
obtaining the blood glucose level and the blood flow index based on the integrated representative waveform.

17. The method of claim 16, wherein the extracting comprises:
segmenting the optical signal of each of the wavelengths into periods to generate a plurality of segmented signals;
obtaining a similarity between the plurality of segmented signals of each of the wavelengths; and
extracting the representative waveforms of each of the wavelengths based on the similarity.

18. The method of claim 16, wherein the generating comprises generating the integrated representative waveform by subtracting or dividing a representative waveform of one wavelength from or by a representative waveform of another wavelength.

19. The method of claim 16, wherein the obtaining the blood glucose level and the blood flow index based on the integrated representative waveform comprises:
extracting a feature from the integrated representative waveform; and
obtaining the blood glucose level and the blood flow index based on the extracted feature.

20. The method of claim 15, wherein the estimating the at least one from among the dietary information and the dietary metabolism state information based on the comparing comprises:
when compared with the pre-stored blood glucose level change and the pre-stored blood flow index change, in response to at least one of a range of a blood glucose level variation and a range of a blood flow index variation being increased by a value equal to or higher than a first threshold value, and the time interval between the peak blood glucose level and the peak blood flow index being changed by a value lower than a second threshold value, estimating that the ingested food has higher carbohydrate; and
when compared with the pre-stored blood glucose level change and the pre-stored blood flow index change, in response to the range of the blood glucose level variation and the range of the blood flow index variation being changed by a value lower than a third threshold value, and the time interval between the peak blood glucose level and the peak blood flow index being increased by a value equal to or higher than a fourth threshold value, estimating that the ingested food has higher fat.

21. The apparatus of claim 15, the estimating the at least one from among the dietary information and the dietary metabolism state information based on the comparing comprises:

when compared with the pre-stored blood glucose level change and the pre-stored blood flow index change, in response to at least one of a range of a blood glucose level variation and a range of a blood flow index variation being increased, or the time interval between the peak blood glucose level and the peak blood flow index being increased, estimating that dietary metabolism state of the object is not positive; and when compared with the pre-stored blood glucose level change and the pre-stored blood flow index change, in response to the at least one of the range of the blood glucose level variation and the range of the blood flow index variation being decreased, or the time interval between the peak blood glucose level and the peak blood flow index being decreased, estimating that the dietary metabolism state of the object is positive.

* * * * *